US009272969B2

(12) United States Patent
Merkel et al.

(10) Patent No.: US 9,272,969 B2
(45) Date of Patent: Mar. 1, 2016

(54) AZEOTROPIC COMPOSITIONS OF 1,3,3-TRICHLORO-1,1-DIFLUOROPROPANE AND HYDROGEN FLUORIDE

(71) Applicant: Honeywell International Inc., Morristown, NJ (US)

(72) Inventors: Daniel C. Merkel, West Seneca, NY (US); Konstantin A. Pokrovski, Orchard Park, NY (US); Hsueh Sung Tung, Getzville, NY (US); Haiyou Wang, Amherst, NY (US); Stephen A. Cottrell, Churchville, NY (US); Hang T. Pham, Amherst, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 13/798,250

(22) Filed: Mar. 13, 2013

(65) Prior Publication Data

US 2014/0264154 A1 Sep. 18, 2014

(51) Int. Cl.
| C07C 19/10 | (2006.01) |
| C23G 1/02 | (2006.01) |
| C23G 5/028 | (2006.01) |
| C11D 7/08 | (2006.01) |
| C11D 7/50 | (2006.01) |

(52) U.S. Cl.
CPC . *C07C 19/10* (2013.01); *C11D 7/08* (2013.01); *C11D 7/5036* (2013.01); *C23G 5/02809* (2013.01)

(58) Field of Classification Search
None
See application file for complete search history.

(56) References Cited

U.S. PATENT DOCUMENTS

| 5,710,352 | A | * | 1/1998 | Tung | 570/166 |
| 5,763,706 | A | | 6/1998 | Tung et al. | |
| 5,811,603 | A | | 9/1998 | Elsheikh | |
| 5,877,359 | A | | 3/1999 | Elsheikh | |
| 6,013,846 | A | | 1/2000 | Wismer et al. | |
| 6,124,511 | A | * | 9/2000 | Ohnishi et al. | 570/167 |
| 6,166,274 | A | | 12/2000 | Chen et al. | |
| 6,191,328 | B1 | * | 2/2001 | Kitano et al. | 570/180 |
| 6,844,475 | B1 | | 1/2005 | Tung et al. | |
| 7,241,928 | B2 | * | 7/2007 | Rao et al. | 570/135 |
| 7,371,363 | B2 | * | 5/2008 | Merkel et al. | 423/488 |
| 8,207,383 | B2 | | 6/2012 | Deur-Bert et al. | |
| 8,309,774 | B2 | | 11/2012 | Pigamo et al. | |
| 8,367,878 | B2 | | 2/2013 | Merkel et al. | |
| 8,704,017 | B2 | * | 4/2014 | Pokrovski et al. | 570/160 |
| 8,754,273 | B2 | * | 6/2014 | Zhai et al. | 570/170 |
| 2002/0143215 | A1 | * | 10/2002 | Tung et al. | 570/161 |
| 2009/0182179 | A1 | * | 7/2009 | Merkel et al. | 570/168 |
| 2009/0227822 | A1 | | 9/2009 | Pham et al. | |
| 2011/0155942 | A1 | | 6/2011 | Pigamo et al. | |
| 2011/0201853 | A1 | | 8/2011 | Tung et al. | |
| 2011/0237846 | A1 | * | 9/2011 | Kawaguchi et al. | 570/165 |
| 2011/0240902 | A1 | | 10/2011 | Merkel et al. | |
| 2011/0295045 | A1 | * | 12/2011 | Hulse et al. | 570/178 |
| 2012/0004474 | A1 | * | 1/2012 | Okamoto | 570/151 |

(Continued)

OTHER PUBLICATIONS

PCT ISR & Written Opinion issued in PCT/US2014/020603 dated Jun. 26, 2014.

*Primary Examiner* — Allan Olsen
(74) *Attorney, Agent, or Firm* — Bruce O. Bradford

(57) ABSTRACT

Provided are azeotropic or azeotrope-like mixtures of 1,3,3-trichloro-1,1-difluoro-propane (HCFC-242fa) and hydrogen fluoride. Such compositions are useful as a feed stock or intermediate in the production of HFC-245fa and HCFO-1233zd.

11 Claims, 1 Drawing Sheet

P-T-X of 242fa/HF at 0 C

(56) References Cited

U.S. PATENT DOCUMENTS

| | | | |
|---|---|---|---|
| 2012/0037843 A1* | 2/2012 | Pham et al. | 252/79.3 |
| 2012/0053371 A1* | 3/2012 | Johnson et al. | 570/156 |
| 2012/0059199 A1* | 3/2012 | Pokrovski et al. | 570/155 |
| 2012/0215039 A1 | 8/2012 | Hulse et al. | |
| 2013/0211154 A1* | 8/2013 | Cottrell et al. | 570/155 |
| 2014/0147343 A1* | 5/2014 | Merkel et al. | 422/187 |

\* cited by examiner

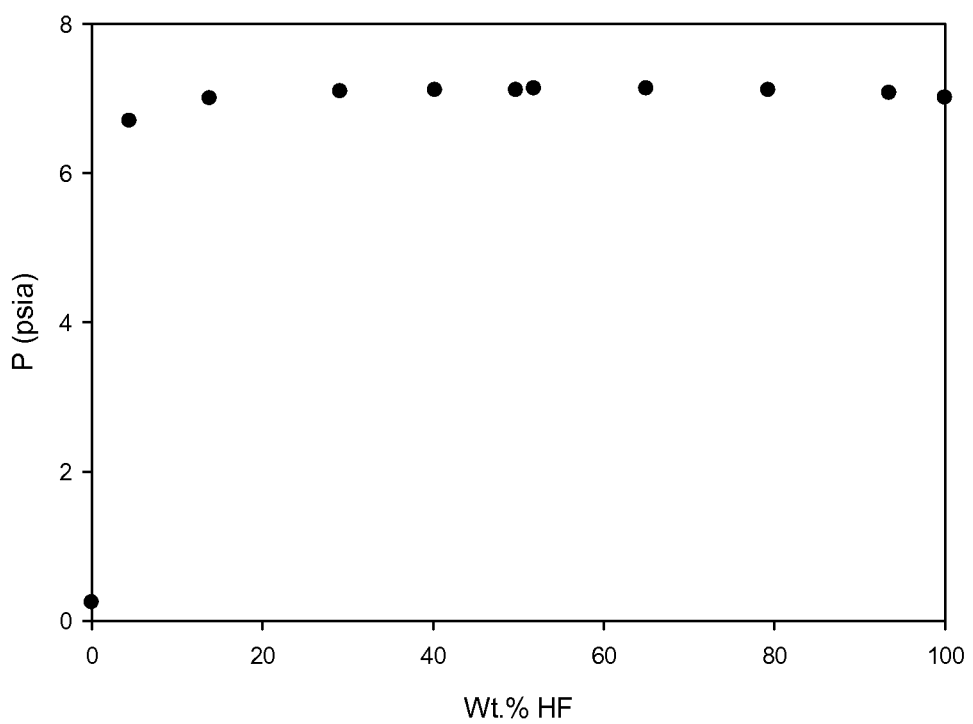

AZEOTROPIC COMPOSITIONS OF 1,3,3-TRICHLORO-1,1-DIFLUOROPROPANE AND HYDROGEN FLUORIDE

FIELD OF THE INVENTION

The present invention pertains to azeotropic or azeotrope-like compositions of 1,3,3-trichloro-1,1-difluoropropane (HCFC-242fa) and hydrogen fluoride (HF).

BACKGROUND OF THE INVENTION

Chlorofluorocarbon (CFC) based chemicals have been widely use in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is consider to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd(E), pure 1233zd(Z), or certain mixtures of the two isomers may be suitable for particular applications as refrigerants, propellants, blowing agents, solvents, or for other uses.

1,3,3-Trichloro-1,1-difluoropropane (HCFC-242fa or simply, 242fa) can be either a starting material or an intermediate (if starting with a less fluorinated chlorocarbon, e.g., HCC-240fa, 1,1,3,3-tetrachloropropene, 1,3,3,3-tetrachloropropene, and/or 1,1,3,3-tetra-chloro-1-fluoropropane) in the production of both 245fa and 1233zd which are well known in the art as described in U.S. Pat. Nos. 5,763,706 and 6,844,475, respectively. In the case of 1233zd, see U.S. Patent Pub. No. 2011-0201853. These documents are hereby incorporated herein by reference.

It has now been found that an important feed stock or intermediate in the production of both 245fa and 1233zd, is an azeotrope or azeotrope-like mixture of 1,3,3-trichloro-1,1-difluoropropane (HCFC-242fa) and hydrogen fluoride (HF). This intermediate, once formed, may thereafter be separated into its component parts by extraction or distillation techniques. HCFC-242fa has a boiling point of about 109° C. and HF has a boiling point of about 20° C., at standard atmospheric pressure. The azeotropic or azeotrope-like compositions find use not only as reactor feeds in the production of 245fa and 1233zd, but they are additionally useful as solvent compositions for removing surface oxidation from metals.

SUMMARY OF THE INVENTION

The invention provides a heterogeneous azeotropic composition consisting essentially of 1,3,3-trichloro-1,1-difluoropropane (242fa) and hydrogen fluoride (HF).

The invention further provides an azeotropic or azeotrope-like composition which consists essentially of from about 90 to about 97 weight percent hydrogen fluoride and from about 10 to about 3 weight percent 1,3,3-trichloro-1,1-difluoropropane (242fa), which composition has a boiling point of about 0° C., at pressure of about 7.1 psia.

The invention also provides a method of forming a heterogeneous azeotropic or azeotrope-like composition which consists essentially of blending from about 1 to about 99 weight percent hydrogen fluoride and from about 99 to about 1 weight percent 1,3,3-trichloro-1,1-difluoropropane (242fa), which composition has a boiling point of about— from 0° C. to about 25° C., at pressure of from about 7.1 psia to about 17.9 psia.

The invention also provides a method of forming a heterogeneous azeotropic or azeotrope-like composition which consists essentially of blending from about 0.2 to about 97 weight percent hydrogen fluoride and from about 99.8 to about 3 weight percent 1,3,3-trichloro-1,1-difluoropropane (242fa), which composition has a boiling point of about from 0° C. and 25° C., at pressure of from about 7.1 to about 17.9 psia.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

FIG. 1 shows a plot of the vapor pressures of the mixtures formed in Example 1 as measured at 0° C.

DETAILED DESCRIPTION OF THE PREFERRED EMBODIMENT

Surprisingly, it has been discovered that when 1,3,3-trichloro-1,1-difluoropropane (242fa) and HF were fed to a reactor, 242fa forms an azeotropic or azeotrope-like mixtures with HF. The unreacted 242fa/HF intermediate was found in the product stream.

The thermodynamic state of a fluid is defined by its pressure, temperature, liquid composition and vapor composition. For a true azeotropic composition, the liquid composition and vapor phase are essentially equal at a given temperature and pressure. In practical terms this means that the components cannot be separated during a phase change.

For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling.

For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures.

Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and 242fa to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with 242fa.

In a preferred embodiment, the inventive composition contains from about 99 to about 1 weight percent HF, preferably from about 95 weight percent to about 5 weight percent and most preferably from about 85 weight percent to about 15 weight percent. In another preferred embodiment, the inventive composition contains from about 1 to about 99 weight percent 242fa preferably from about 5 weight percent to about 95 weight percent and most preferably from about 15 weight percent to about 85 weight percent.

The compositions of the present invention have a boiling point of about 0° C. at a pressure of about 7.1 psia. An azeotropic or azeotrope-like composition having about 89±2 weight percent HF and about 11±2 weight percent 242fa has been found to boil at about 0° C. and 7.1 psia.

The following non-limiting examples serve to illustrate the invention.

EXAMPLE 1

12.2 g of 1,3,3-trichloro-1,1-difluoropropane (HCFC-242fa) were combined with 13.2 g of HF to form a heterogeneous azeotrope mixture. This experiment was done at 0° C., and at 7.1 psia (by visual observation).

EXAMPLE 2

Binary compositions containing solely 1,3,3-trichloro-1,1-difluoropropane (HCFC-242fa) and HF are blended to form a heterogeneous azeotrope mixtures at different compositions.

The vapor pressures of the mixtures are measured at 0° C. and the following results are noticed.

Table 1 shows the vapor pressure measurement of 242fa and HF as a function of composition of weight percent HF at constant temperatures of about 0° C.

TABLE 1

| P-T-X of 242fa/HF at T = 0° C. | |
|---|---|
| Wt. % HF | P (Psia) |
| 0.0 | 0.2 |
| 4.4 | 6.7 |
| 13.8 | 7.0 |
| 29.1 | 7.1 |
| 40.3 | 7.1 |
| 49.7 | 7.1 |
| 51.9 | 7.1 |
| 65.0 | 7.1 |
| 79.3 | 7.1 |
| 93.5 | 7.1 |
| 100.0 | 7.0 |

These data also show that the mixture is an azeotrope since the vapor pressures of mixtures of 242fa and HF are higher, at all indicated blend proportions, than 242fa and HF alone, i.e. as indicated in the first and last rows when HF is 0.0 wt % and 242fa is at 100.0 wt % as well as when 242fa is at 0.0 wt % and HF is at 100.0 wt. %. The data from Table 1 are shown in graphic form in FIG. 1.

EXAMPLE 3

The azeotropic composition of the 242fa/HF mixture is also verified by Vapor-Liquid—Liquid Equilibrium (VLLE) experiment. 13.9 g of 1,3,3-trichloro-1,1-difluoro-propane (HCFC-242fa) were combined with 13.7 g of HF to form a heterogeneous mixture (visual observation) at 0° C. The vapor compositions of the mixture were sampled at a temperature of 0° C. and at pressure of 7.1 psia. The result shows that the azeotropic composition is about 89±2 wt % HF at 0° C.

This mixture is observed to be heterogeneous azeotrope at temperature of 0° C. and pressure of 7.1 psia.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An isolated composition consisting essentially of 1,3,3-trichloro-1,1-difluoropropane (242fa) and hydrogen fluoride, wherein the percentage of HF is between 13.8 and 29.1 weight percent, wherein the composition exhibits azeotropic or azeotrope-like properties and wherein the mixture is useful as a feed stock for the production of HCFO-1233zd, which composition heterogeneous and has a boiling point of from about 0° C. to about 25° C., at a pressure of from about 7.1 psia to about 17.9 psia.

2. The composition of claim 1, which composition has a boiling point of about 0° C., at a pressure of about 7.1 psia.

3. An isolated binary composition consisting of a mixture of 1,3,3-trichloro-1,1-difluoropropane (242fa) and hydrogen fluoride, wherein the composition exhibits azeotropic or azeotrope-like properties and wherein the vapor pressure of the mixture is 7.1 psia at 0° C. and the percentage of HF in the mixture is selected from the group consisting of 29.1, 40.3, 49.7, 51.9, 65.0, 79.3 and 93.5 weight percent, and wherein the mixture is useful as a feed stock for the production of HCFO-1233zd.

4. The composition of claim 3, wherein the percentage of HF in the mixture is 29.1 weight percent.

5. The composition of claim 3, wherein the percentage of HF in the mixture is 40.3 weight percent.

6. The composition of claim 3, wherein the percentage of HF in the mixture is 49.7 weight percent.

7. The composition of claim 3, wherein the percentage of HF in the mixture is 51.9 weight percent.

8. The composition of claim 3, wherein the percentage of HF in the mixture is 65.0 weight percent.

9. The composition of claim 3, wherein the percentage of HF in the mixture is 79.3 weight percent.

10. The composition of claim 3, wherein the percentage of HF in the mixture is 93.5 weight percent.

11. An isolated binary composition consisting of a heterogeneous mixture of 1,3,3-trichloro-1,1-difluoropropane (242fa) and hydrogen fluoride, and wherein the azeotropic composition is about 89±2 wt % HF at 0° C.

* * * * *